(12) United States Patent
Batra et al.

(10) Patent No.: US 8,945,027 B2
(45) Date of Patent: Feb. 3, 2015

(54) HEATED COMPRESSION THERAPY SYSTEM AND METHOD

(76) Inventors: Munish K. Batra, Rancho Santa Fe, CA (US); Ronald J. Koch, Columbus, OH (US)

( * ) Notice: Subject to any disclaimer, the term of this patent is extended or adjusted under 35 U.S.C. 154(b) by 281 days.

(21) Appl. No.: 13/188,434

(22) Filed: Jul. 21, 2011

(65) Prior Publication Data

US 2012/0283607 A1 Nov. 8, 2012

Related U.S. Application Data

(60) Provisional application No. 61/385,810, filed on Sep. 23, 2010.

(51) Int. Cl.
*A61F 7/00* (2006.01)
*A61H 9/00* (2006.01)
*A61F 7/08* (2006.01)

(52) U.S. Cl.
CPC ............. *A61F 7/007* (2013.01); *A61H 9/0078* (2013.01); *A61H 9/0092* (2013.01); *A61F 7/08* (2013.01); *A61H 2201/0107* (2013.01); *A61H 2201/0207* (2013.01); *A61H 2201/0228* (2013.01); *A61H 2201/0278* (2013.01); *A61H 2201/5082* (2013.01); *A61H 2209/00* (2013.01); *A61F 2007/0091* (2013.01); *Y10S 601/02* (2013.01)
USPC ............ 601/15; 601/64; 601/DIG. 2; 607/96; 607/104; 602/14

(58) Field of Classification Search
CPC ... A61H 1/00; A61F 7/007; A61F 2007/0071; A61F 2007/0076; A61F 13/046
USPC ................ 601/15, 18, 55, 61, 64, 88, 105, 601/148–152, DIG. 1, DIG. 2; 602/13–14; 128/DIG. 20; 607/96, 104, 114
See application file for complete search history.

(56) References Cited

U.S. PATENT DOCUMENTS

| | | | | |
|---|---|---|---|---|
| 4,279,255 A | * | 7/1981 | Hoffman | 607/112 |
| 4,453,538 A | | 6/1984 | Whitney | |
| 4,702,235 A | * | 10/1987 | Hong | 602/13 |
| 5,074,285 A | * | 12/1991 | Wright | 601/15 |
| 5,230,335 A | | 7/1993 | Johnson, Jr. | |
| 5,269,023 A | * | 12/1993 | Ross | 2/66 |
| 5,335,506 A | | 8/1994 | Byoung-moo | |
| 5,407,421 A | * | 4/1995 | Goldsmith | 602/5 |
| 5,584,798 A | * | 12/1996 | Fox | 601/152 |
| 5,605,144 A | * | 2/1997 | Simmons et al. | 126/204 |
| 5,697,962 A | * | 12/1997 | Brink et al. | 607/108 |
| 5,795,312 A | | 8/1998 | Dye | |
| 6,197,045 B1 | | 3/2001 | Carson | |
| 6,592,534 B1 | | 7/2003 | Rutt | |
| 6,960,226 B2 | | 11/2005 | Ward | |
| 7,179,242 B2 | | 2/2007 | Belzidsky | |

(Continued)

FOREIGN PATENT DOCUMENTS

WO WO/2007/120639 A2 10/2007
WO WO/2007/120639 A3 10/2007

*Primary Examiner* — Justine Yu
*Assistant Examiner* — Christopher Miller
(74) *Attorney, Agent, or Firm* — Ronald J. Koch

(57) ABSTRACT

A calf garment assembly having, a calf garment having an internal chamber and being substantially airtight and being in fluid communication with a pressurized air source, and a heating element working in conjunction with the calf garment to provide heated DVT therapy.

4 Claims, 5 Drawing Sheets

(56) References Cited

U.S. PATENT DOCUMENTS

| | | |
|---|---|---|
| 7,744,551 B2 * | 6/2010 | Pick et al. .................. 602/5 |
| 7,959,588 B1 * | 6/2011 | Wolpa .............................. 602/13 |
| 2005/0033392 A1 | 2/2005 | Belzidsky |
| 2005/0143797 A1 * | 6/2005 | Parish et al. .................. 607/104 |
| 2005/0165463 A9 | 7/2005 | Belzidsky |
| 2006/0016012 A1 | 1/2006 | Liu |
| 2007/0088235 A1 * | 4/2007 | Tseng ........................... 601/151 |
| 2007/0129658 A1 * | 6/2007 | Hampson et al. ............... 602/13 |
| 2007/0142764 A1 | 6/2007 | Belzidsky |
| 2007/0162096 A1 * | 7/2007 | Zakuto et al. .................. 607/104 |
| 2007/0197943 A1 * | 8/2007 | Hakonson et al. .............. 602/13 |
| 2008/0058911 A1 | 3/2008 | Parish |
| 2008/0064992 A1 | 3/2008 | Stewart |
| 2008/0132816 A1 | 6/2008 | Kane |
| 2009/0020521 A1 * | 1/2009 | Blaszczykiewicz et al. . 219/529 |
| 2009/0069731 A1 * | 3/2009 | Parish et al. ................... 601/150 |
| 2010/0089897 A1 * | 4/2010 | Bart .............................. 219/211 |
| 2010/0152821 A1 * | 6/2010 | Rein et al. ....................... 607/96 |
| 2010/0268130 A1 * | 10/2010 | Khan .............................. 601/46 |
| 2011/0077723 A1 | 3/2011 | Parish et al. |

* cited by examiner

HEATED COMPRESSION THERAPY SYSTEM AND METHOD

CLAIM OF PRIORITY BASED ON COPENDING APPLICATION

Claims benefit of provisional application no. 61/385,810

CROSS REFERENCE TO RELATED APPLICATIONS

Provisional application no. 61/385,810

FEDERALLY SPONSORED RESEARCH

Not Applicable

SEQUENCE LISTING, TABLE, OR COMPUTER PROGRAM COMPACT DISK APPENDIX

Not Applicable

The present application is related to the co-pending provisional patent application No. 61/385,810 of Munish K. Batra, et al, filed on Sep. 23, 2010, entitled "Heated Compression Therapy System and Method", and based on which priority is herewith claimed under 35 U.S.C. 119(e) and the disclosure of which is incorporated herein by reference in its entirety as if fully rewritten herein.

BACKGROUND AND SUMMARY

The present invention relates generally to systems and methods for minimizing or preventing deep vein thrombosis (DVT) and maintaining the body temperature of a person under anesthesia, and specifically to systems and methods that incorporate applying heat and compression in furtherance thereof.

Deep vein thrombosis (DVT) relates to the forming of blood clots (thrombi) in the deep veins of the body, usually in the pelvis, thigh, or calf. This can result in severe complications—including death. One of the causes of DVT is surgery. The body of an anesthetized person undergoing surgery loses the ability to regulate temperature because the body is paralyzed. The operating room is preferably maintained at lower temperatures. Thus, body temperature drops as a result. This drop in temperature increases the risk of DVT and increases post-operative recovery time (i.e. length of time outpatient must wait before being released). The body temperature of an anesthetized person can fall as low as 92 deg F. It is preferable to maintain the body at around 98.6 during surgery.

Various solutions (aka DVT therapy systems) have been proposed to maintain the body temperature during surgery. For example, an air filled blanket has been used wherein heated air is delivered. One such systems is the "BAIR HUGGER™ Warming Blanket", sold by Cardinal Health. Such solutions are problematic because the blanket and interconnecting hoses are relatively large and cumbersome and tend to interfere with the surgeon needing access to various parts of the body. Additionally, the large, inefficient apparatus used to heat and deliver pressurized air wastes heat that results in a detrimental increase in room temperature.

Another solution involves applying intermittent (pulsed) compression to the calf by wrapping a fluid filled bladder (contained within a fabric sleeve—aka calf garment) around the calf. One such system is the VASOPRESS™ sold by Compression Therapy Concepts utilizing a calf garment model "VP 501M", and compressor model number "VP 500". The foregoing is also collectively referred to herein as a "compression system" or "DVT therapy system", etc.

Some systems have been modified to apply heat to the fluid. However, such systems are inefficient because the heat must be transferred to the fluid, then delivered to the bladder, then transferred from the bladder to the calf.

The present invention overcomes the foregoing problems as well as achieves other objects and advantages that will be apparent to those of skill in the art by utilizing a heating element (flexible heating pad, or air-activated heat pack) in conjunction with a compression bladder.

In one embodiment, an electrically energized flexible heating pad is used. The flexible pad is electrically heated and thus it delivers heat more efficiently than fluid based systems because the conventional intermediate heat transfer medium (fluid) is eliminated. The heating pad is restrained against the inside of the bladder/sleeve combination by a removable, disposable sheet situated between the skin and the bladder. The heating pad can therefore be reused because it does not come in contact with the skin. The sheet and bladder are discarded.

Flexible heating pads are known. One such device is the "Flexible Silicone Rubber Fiberglass Insulated Heater" sold by OMEGA ENGINEERING, INC™. They come in rectangular or round shapes in varying wattage per square inch and are available in either alternating or direct current configurations. Additionally, they can be driven by either varying or pulsed voltages. The flexible heating pad is advantageous because it can wrap around the calf and move along with the intermittent compressions of the compression system.

It is essential that a safe surface temperature be maintained to prevent injury to the anesthetized patient who is unable to communicate. The surface temperature of the flexible heating pads can exceed 400 deg F. It is preferred to establish a temperature threshold at 105 deg F. to prevent injury. The electrical energy used to heat the pad is regulated to achieve this. The temperature of the heating pad is regulated by a feedback loop which incorporates a temperature probe placed against the patient's leg. Alternatively, a temperature probe and shutoff circuit is employed.

Although not essential, it is advantageous to use a low, direct current voltage to energize the heating pad. This is advantageous because conventional 60 hertz AC power can interfere with the body's nervous and cardio vascular systems. It is also advantageous (but not essential) to provide electrical energy from a battery. This is advantageous because the battery/heating pad system is electrically isolated thus reducing the chance of shocking the patient.

The air-activated heat pack fits inside of the air bladder and is activated and heated as pressurized air is intermittently applied. Air-activated heat packs are known in the art. A popular variety utilizes iron, water, cellulose, vermiculite, activated carbon, and salt. An example of such a heat pack is the GRABBER™ brand (www.warmers.com). These heat packs are nicely applied to conventional DVT therapy systems that utilize pressurized air (e.g. intermittent (pulsed) compression systems). The air delivery of these systems serves an additional purpose. Exposure to the pressurized air causes the heat pack to heat up without the need for externally (e.g. electrical pad, heated fluid) generated heat. This offers several advantages including eliminating the risk of electrical shock and connection wires, and also cost effectiveness.

The present invention incorporates air-activated heat packs with conventional pressurized air DVT therapy systems to provide a cost effective, efficient means of adding heat to pressurized therapy. The heat packs are contained within the air bladder (aka internal chamber) of the calf garment. The combination must be stored, until just prior to use, in an air-tight package to prevent premature activation.

DETAILED DESCRIPTION

Figure 1:
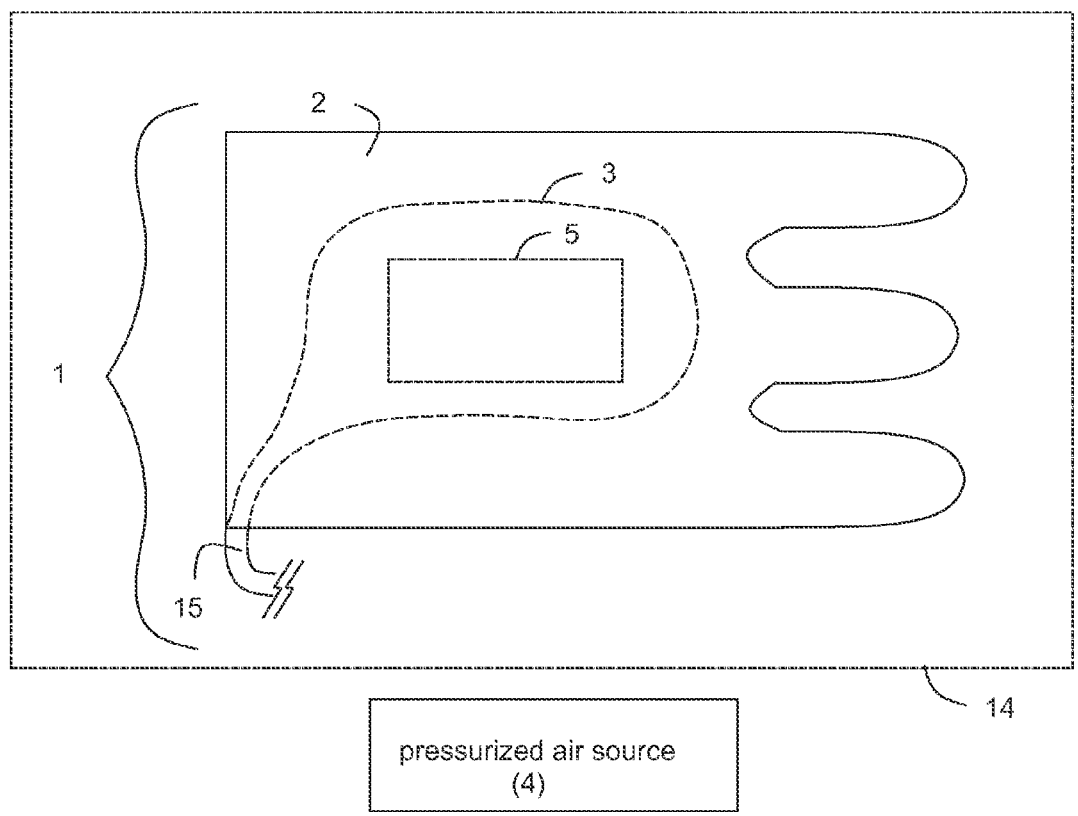
FIG. 1 depicts a block diagram of one embodiment of the invention
Figure 2:
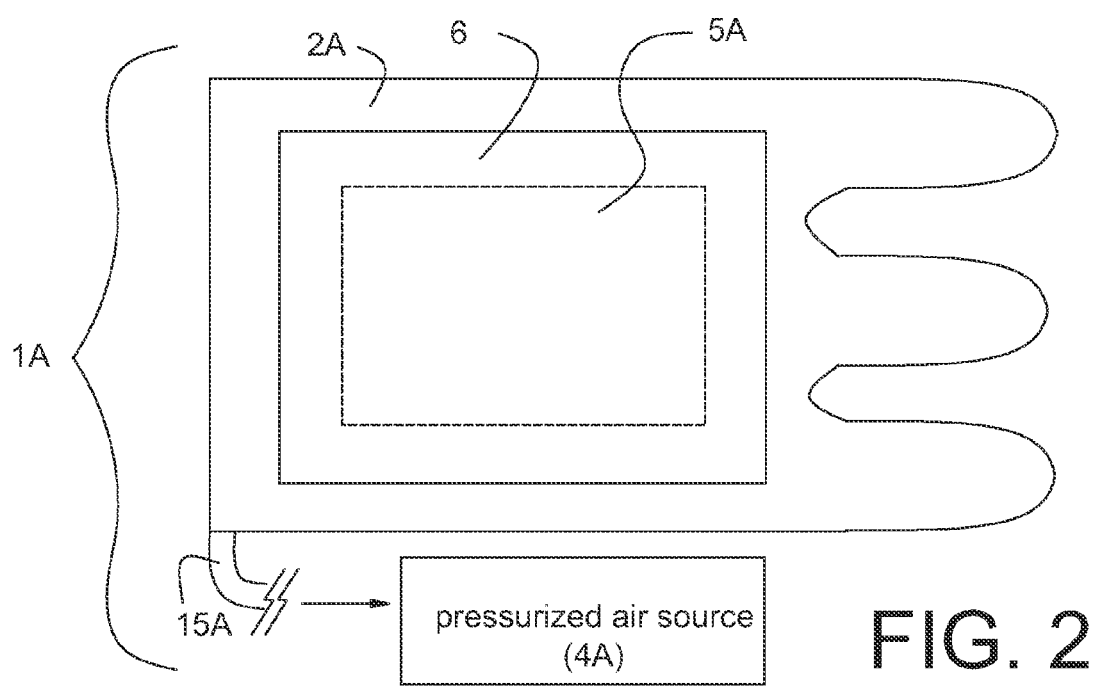
FIG. 2 depicts a block diagram of an alternative embodiment of the invention
Figure 3:
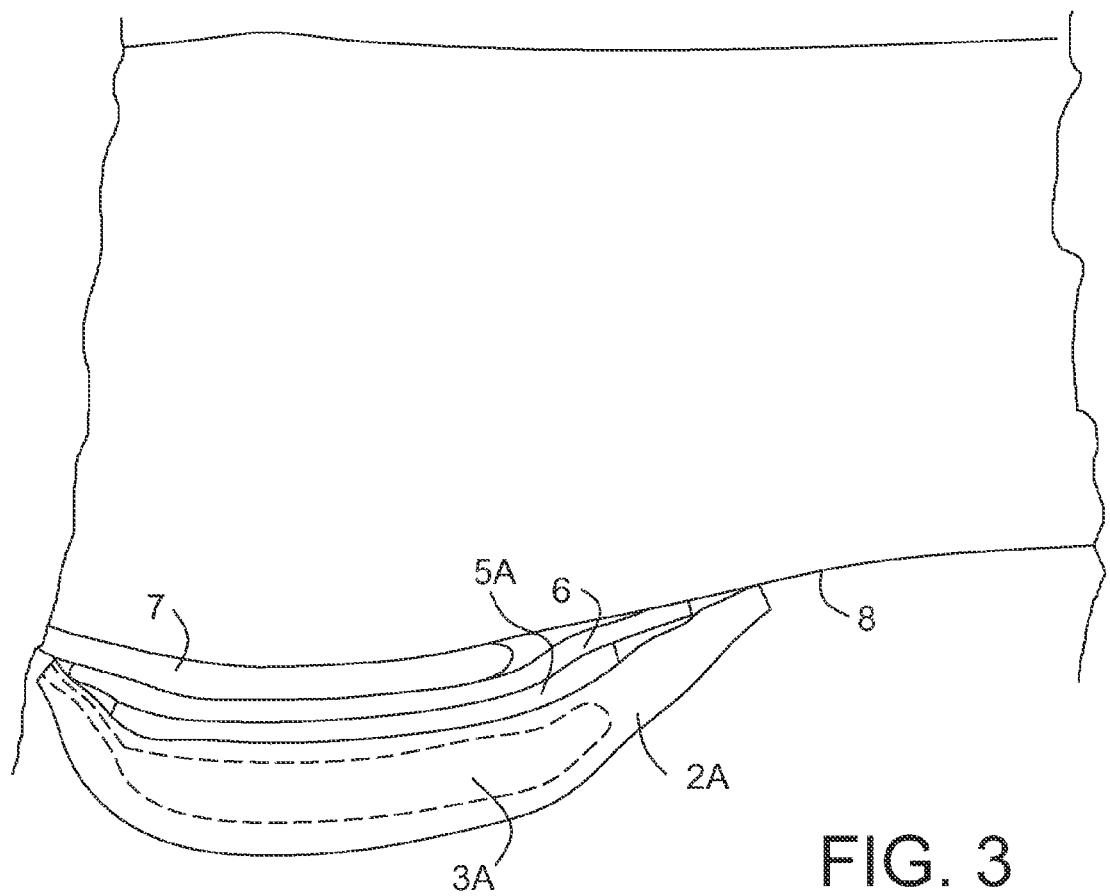
FIG. 3 depicts a cross sectional fragmentary view of an alternative embodiment of the invention

In various embodiments, a calf garment assembly 1, 1A comprises, calf garment 2, 2A having internal chamber 3, 3A being substantially airtight and being in fluid communication with pressurized air source 4, 4A, and heating element 5, 5A being restrained proximate calf garment 2, 2A, respectively.

Referring now to FIG. 1, heating element 5 can be either securedley attached within internal chamber 3, or alternatively can be loosely inserted within. If the latter, the positioning of heating element 5 can vary relative to a patient's leg while in use. Fixing the heating pad within internal chamber 3 allows a more predictable result.

In operation, calf garment assembly 1 is sealed in airtight package 14, to ensure heating element 5 (air-activated heat pack) is not activated by premature exposure to air. Calf garment assembly 1 is removed from airtight package 14 just prior to use. Port 15 of internal chamber 3 of calf garment 2 is connected to pressurized air source 4. Calf garment 2 is then wrapped around calf 8 of a patient. Air is then delivered to air-activated heat pack 5 via internal chamber 3 of calf garment 2 as the bladder is intermittently pressurized.

Referring now to FIGS. 2-5, heating element 5A is restrained to the inside of calf garment 2A by detachable sheet 6. One effective method of attachment is using hook and loop fasteners. Temperature probe 7 is placed adjacent to the skin of a patient 8 and held in place by calf garment 2A. Power regulator 9 (aka electrical feedback circuit or electrical power regulator) is in electrical communication with temperature probe 7, heating element 5A, and power source 10. Power regulator 9 is operative to regulate energy delivery from power source 10 to heating element 5A proportional to the output of temperature probe 7.

Figure 4:
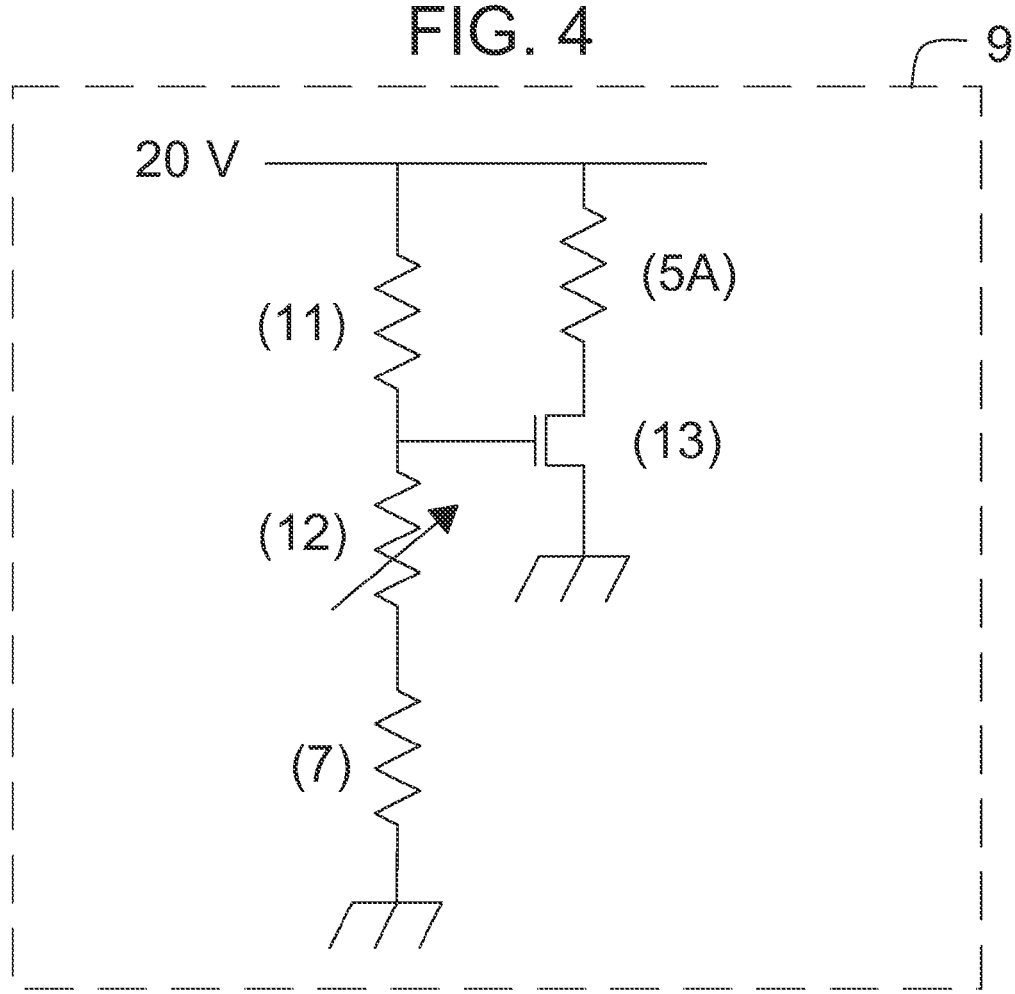
FIG. 4 depicts a schematic diagram of one embodiment of a feedback circuit
Figure 5:
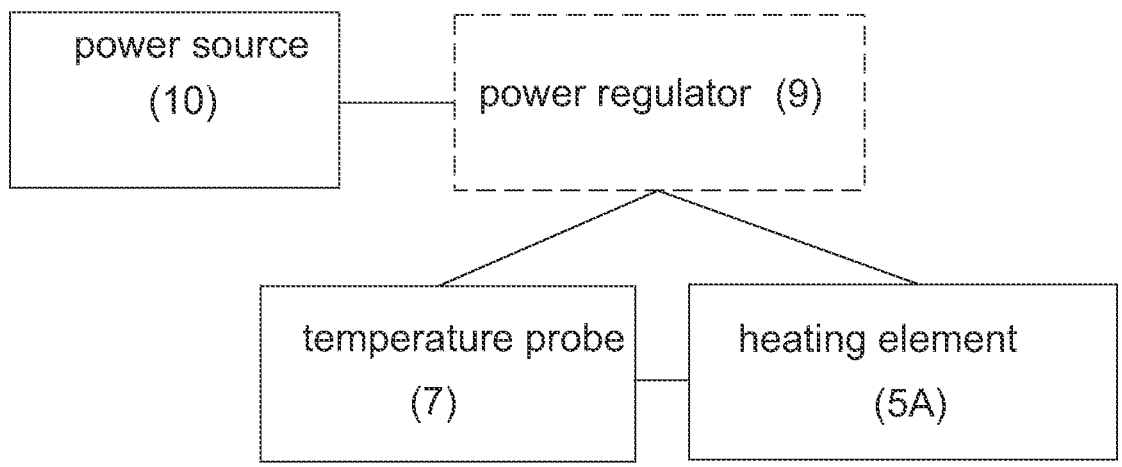
FIG. 5 depicts a block diagram of an alternative embodiment of the invention

In one embodiment, power regulator 9 comprises the schematic of FIG. 4 wherein resistor 11 is 20 kilo-ohms, variable potentiometer 12 is 10 kilo-ohms, temperature probe 7 is a standard esophageal/rectal temperature probe (thermistor), heating element 5A is a rectangular silicone rubber heater (7 inches by 5 inches & 5 Watts per square inch), transistor 13 is an N-Channel IFR510 Power MOSFET, and power source 10 supplies 20 volts DC to the circuit.

Each of such circuits drives one calf garment. Two calf garments are typically utilized (one for each leg), which requires two such circuits. Potentiometer 12 is varied (as can be the voltage supplied) to calibrate the system so as to prevent excessive (e.g. >105 deg F.) temperature exposure to the patient's leg. The resistance of probe 7 varies with temperature. The change in resistance regulates transistor 13 to vary the current through heating element 5A. In another embodiment, a shutoff circuit is employed to completely de-energize heating element 5A when a given temperature (e.g. 105 deg F.) is reached.

It is to be understood that a calf garment can be comprised of one or more chambers (aka air bladder, etc) and that air-activated heat packs can be applied to some or all of them. Effective heat delivery is accomplished by placing the heat packs so as to maximize proximity to the patient's calf. In other words, placement of heat packs at locations that are not in direct contact with the leg are inefficient. In one embodiment, a heat pack is securely attached by adhesive or the like to the interior of the chamber. Additionally, the flexible heating pad 5A can be positioned directly over multi bladder systems.

The size and number of air-activated heat packs can be changed to achieve desired temperatures (e.g. to ensure temperature does not exceed 105 deg F.). The active ingredients of the air-activated heat pack can be disbursed in varying thicknesses throughout the inside of the internal chamber to achieve certain heat characteristics. Additionally, the size and wattage of flexible heating pads can be varied for the same purpose.

It is not essential that the internal chamber by completely airtight. The chamber expands upon being pressurized thus applying compression to a patient's leg. The pressure is intermittently supplied to effect an on-off cycle. Thus, the chamber is depressurized (either passively or actively) during the off cycle and small amounts of air leakage do not compromise this functionality.

Conventional calf garments are typically made of latex-free flexible materials of varying types. The choice of material and thickness thereof can be varied to achieve certain heat characteristics. For instance, thicker garment material can be utilized to impede heat flow and ensure safe temperatures at the patient's leg.

The internal chamber of the calf garment has a port for fluid communication with a pressurized air source. It is to be understood that such a port, or functional equivalent, is included in all the described embodiments, but that in some instances the port is utilized only for pressurizing the chamber and not for activating a heat pack.

What is claimed is:

1. A calf garment assembly comprising,
   a calf garment having an internal chamber being substantially airtight and being in fluid communication with a pressurized air source;
   an air-activated heat pack being entirely within the internal chamber of the calf garment and;
   the air-activated heat pack being selectively activated by the pressurized air source without the need for externally generated heat.

2. The calf garment assembly of claim 1 further comprising:
   the air-activated heat pack being securely attached within the internal chamber of the calf garment.

3. A method for administering heated compression therapy comprising the steps of:
   providing a calf garment assembly sealed in an airtight package, the calf garment assembly comprising,
   a calf garment having an internal chamber being substantially airtight and having a port for fluid communication with a pressurized air source,
   and an air-activated heat pack being restrained entirely within the internal chamber of the calf garment;
   removing the calf garment assembly from the airtight package;

connecting the port of the internal chamber of the calf garment to a pressurized air source;
wrapping the calf garment around the calf of a patient;
whereby air is delivered to the internal chamber, and the air-activated heat pack is selectively activated by the pressurized air source.

4. The method of claim 3 further comprising:
the air-activated heat pack being securedly attached within the internal chamber of the calf garment.

* * * * *